(12) United States Patent
Straub

(10) Patent No.: US 7,439,408 B2
(45) Date of Patent: Oct. 21, 2008

(54) METHOD FOR PRODUCING HALOGENATED 2-(3-BUTENYLSULPHANYL)-1,3-THIAZOLES

(75) Inventor: Alexander Straub, Wuppertal (DE)

(73) Assignee: Bayer Cropscience AG, Monheim (DE)

( * ) Notice: Subject to any disclaimer, the term of this patent is extended or adjusted under 35 U.S.C. 154(b) by 158 days.

(21) Appl. No.: 11/403,743

(22) Filed: Apr. 13, 2006

(65) Prior Publication Data

US 2006/0183915 A1 Aug. 17, 2006

Related U.S. Application Data

(62) Division of application No. 10/501,115, filed as application No. PCT/EP03/00028 on Jan. 3, 2003, now Pat. No. 7,078,527.

(30) Foreign Application Priority Data

Jan. 15, 2002 (DE) ............................... 102 01 238

(51) Int. Cl.
*C07C 21/18* (2006.01)
(52) U.S. Cl. ........................ 570/153; 570/123
(58) Field of Classification Search ................ 570/123, 570/153
See application file for complete search history.

(56) References Cited

U.S. PATENT DOCUMENTS

| | | | | |
|---|---|---|---|---|
| 2,426,397 | A | 8/1947 | Jones | 260/302 |
| 3,510,503 | A | 5/1970 | Brokke et al. | 260/455 |
| 3,513,172 | A | 5/1970 | Brokke | 260/302 |
| 3,689,662 | A * | 9/1972 | Brokke et al. | 514/478 |
| 3,697,538 | A | 10/1972 | Boocock et al. | 260/309 |
| 4,748,186 | A * | 5/1988 | Cullen et al. | 558/4 |
| 4,952,580 | A | 8/1990 | Martinez et al. | 514/236.2 |
| 5,705,516 | A | 1/1998 | Turnbull et al. | 514/376 |
| 5,728,833 | A | 3/1998 | Turnbull et al. | 544/309 |
| 5,912,243 | A | 6/1999 | Dowlingt et al. | 514/241 |
| 5,914,423 | A | 6/1999 | Turnbull et al. | 558/54 |
| 5,952,359 | A | 9/1999 | Godfrey et al. | 514/369 |
| 5,994,553 | A | 11/1999 | Harada et al. | 548/182 |
| 6,156,904 | A | 12/2000 | Bowden et al. | 548/182 |
| 6,248,137 | B1 | 6/2001 | Terranova et al. | 8/409 |
| 6,734,198 | B1 | 5/2004 | Watanabe et al. | 514/369 |
| 7,078,527 | B2 * | 7/2006 | Straub | 548/182 |
| 2001/0020310 | A1 | 9/2001 | Terranova et al. | 8/405 |

FOREIGN PATENT DOCUMENTS

| | | |
|---|---|---|
| EP | 0 926 140 | 6/1999 |
| GB | 2304713 | 3/1997 |
| GB | 2 322 372 | 8/1998 |
| WO | 88/00183 | 1/1988 |

OTHER PUBLICATIONS

Z. Anorg. Allg. Chem., 365, (month unavailable) 1969, pp. 70-78, G. Gattow et al, "Untersuchungen über Dithiocarbamidsäure SC(SH)(NH₂) 2. Verhalten der Dithiocarbamidsäure in wäßriger Lösung".

Z. Anorg. Allg. Chem., 364, (month unavailable) 1969, pp. 161-176, G. Gattow et al, "Untersuchungen über Dithiocarbamidsäure SC(SH)(NH₂) 1. Darstellung und Eighenschaften der freien Säure".
Org. Synth. Coll., vol. 3, (month unavailable) 1955, pp. 763-767, E. Redemann et al, "Rhodanine".
Bull. Soc. Chim. Fr., 3, (month unavailable) 1969, pp. 3001-3002, Jean-Louis Fourquet, "Sur la preparation de l'acide dithicarbamique et du dithiocarbamique et du dithiocarbamate de pyridinium".
Z. Anorg. Allg. Chem., 368, (month unavailable) 1969, pp. 127-132, V. Hahnkamm et al, "Untersuchungen über Dithiocarbamidsäure SC(SH)(NH₂) 3. Alkalimetalldithiocarbamate M[SC(S)(NH₂)]".
Chem. Pharm. Bull., 31, (month unavailable) 1983, pp. 3424-3445, Ryozo Maeda et al, "Studies on the Synthesis and Analgesic and Anti-Inflammatory Activities of 2-Thiazolylamino- and 2-Thiazolyloxyarylacetic Acid Derivatives".
Synthesis, (month unavailable) 1985, pp. 948-949, L. Brandsma et al, "An Efficient Synthesis of 1,3-Thiazole".
J. Med. Chem. 25, (month unavailable) 1982, pp. 1235-1240, Fadia El-Fehail Ali et al, "Imidodisulfamides. 2. Substituted 1,2,3,4-Tetrahydroisoquinolinylsulfonic Imides as Antagonists of Slow-Reacting Substance of Anaphylaxis".
Houben-Weyl, Methoden der Organischen Chemie, vol. IX, pp. 857-867, M. Bögemann et al, "Thiocyansäureester".
Patent Abstracts of Japan & JP 59 155355 A (Shionogi & Co ltd), Sep. 4, 1984.
C.L. Jenkins, J.K. Kochi: Journal of Organic Chemistry, vol. 36, No. 21, 1971, pp. 3103-3111, XP002243668 Herstellung von Allylcarbinyl Thiocyanate, S. 3110.
M.T. Bogert: Journal of the American Chemical Society, vol. 25, 1903, pp. 289-291, XP002243669.

* cited by examiner

*Primary Examiner*—Golam M. M. Shameem
(74) *Attorney, Agent, or Firm*—Browdy and Neimark

(57) ABSTRACT

The present invention relates to a process for preparing a compound of formula (V)

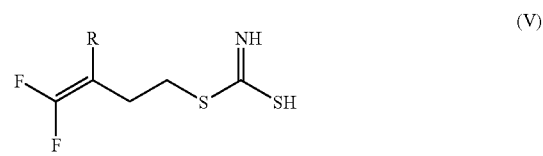

where R is H or F,
by reacting a compound of formula (IV)

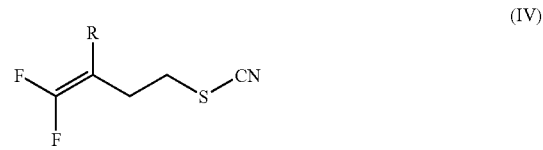

where R is H or F,
with hydrogen sulphide or salts thereof, optionally in the presence of a reaction auxiliary and optionally in the presence of a diluent.

6 Claims, No Drawings

METHOD FOR PRODUCING HALOGENATED 2-(3-BUTENYLSULPHANYL)-1,3-THIAZOLES

This application is a division of U.S. application Serial No. 10/501,115, filed Jan. 26, 2005 now U.S. Pat. No. 7,078,527, which was filed under 35 U.S.C. 371 as a national stage application of PCT/EP03/00028, filed Jan. 3, 2003, which was published in German as International Patent Publication WO 03/059896 on Jul. 24, 2003, which is entitled to the right of priority of German Patent Application 102 01 238.5, filed Jan. 15, 2002.

The present invention relates to a process for preparing halogenated 2-(3-butenylsulphanyl)-1,3-thiazoles of the formula (I)

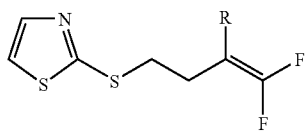

where
R is H or F.

2-[(3-Butenyl)sulphanyl]-1,3-thiazoles of the formula (1) are important precursors for preparing pesticides, as described, for example, in WO 01/02378, U.S. Pat. No. 3,513, 172, U.S. Pat. No. 3,697,538 or WO 95/24403. The compound 2-[(3,4,4-trifluoro-3-butenyl)sulphanyl]-1,3-thiazole was described in WO 86/07590. The compound 2-[(4,4-difluoro-3-butenyl)sulphanyl]-1,3-thiazole was described, for example, in WO 95/24403.

2-[(3,4,4-Trifluoro-3-butenyl)sulphanyl]-1,3-thiazole and 2-[(4,4-difluoro-3-butenyl)sulphanyl]-1,3-thiazole have been prepared hitherto according to WO 86/07590 by metallation of thiazole using n-butyllithium, reaction with elemental sulphur and subsequent reaction with 4-bromo-1,1,2-trifluoro-1-butene (see Ex. 16 of WO 86/07590) or by akylation of 2-mercaptothiazole using 4-bromo-1,1,2-trifluoro-1-butene (see also WO 01/02378). A corresponding approach is also pursued in preparing 2-[(4,4-difluoro-3-butenyl)sulphanyl]-1,3-thiazole (see WO 98/47884 or WO 95/04727).

For the Preparation of the 2-mercapto-1,3-thiazole precursor required, a series of processes have already been described (WO 98/37074, EP 0 926 140 A1, U.S. Pat. No. 5,994,553, U.S. Pat. No. 2,426,397, Mathes et al. (1948), *J. Am. Chem. Soc.* 70, 1451).

Each of the processes described involves the reaction of a salt of dithiocarbamic acid, in particular ammonium dithiocarbamate, with an aqueous solution of chloroacetaldehyde under acidic or neutral conditions.

However, these dithiocarbamates and acids thereof are unstable (Gattow et al. (1969) *Z. Anorg. Allg. Chem.* 365, 70; Gattow and Hahnkamm (1969), *Z. Anorg. Allg. Chem.* 364, 161; Redemann et al. (1955) *Org. Synth. Coll. Vol.* 3, 763; Fourquet (1969) *Bull. Soc. Chim. Fr.* 3, 3001; Hahnkamm et al. (1969) *Z. Anorg. Allg. Chem.* 368, 127). This has the consequence that secondary reactions can occur to a considerable extent and may lead to the release of the dangerous carbon disulphide. The yields are correspondingly poor. In addition, the synthesis of ammonium dithiocarbamate is associated with the use of dangerous carbon disulphide and gaseous ammonia.

It is accordingly an object of the present invention to develop a process which presents an alternative to the processes mentioned and leads directly to the desired end products of the formula (I) while circumventing the intermediate 2-mercapto-1,3-thiazole.

It was known that aryl thiocyanates can be converted by means of hydrogen sulphide to S-aryl dithiocarbamates and that the latter may be cyclized using chloro-acetaldehyde diethyl acetal to give 2-arylmercaptothiazoles (Maeda et al. (1983), *Chem. Pharm. Bull.* 31, 3424, see Chart 3, VII). The cyclization of methyl dithio-carbamate with chloroacetaldehyde is likewise a well-known reaction (Brandsma et al. (1985) *Synthesis,* 948). The compound of the formula V mentioned below where R is F is disclosed by U.S. Pat. No. 3,510,503.

It has been found that compounds of the formula (I) may be prepared by
(a) reacting a compound of the formula (II)

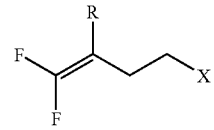

where
R is H or F and
X is bromine, chlorine, mesylate or tosylate, and is preferably bromine,
with a thiocyanate salt of the formula (III)

$$M^+SCN^-$$ (III)

where
$M^+$ is hydrogen, an ammonium ion, a tetraalkylammonium ion or an alkali metal ion, e.g. $K^+$ or $Na^+$,
to give 3-butenyl thiocyanates of the formula (IV)

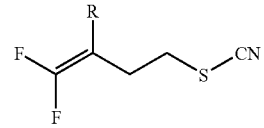

where
R is as defined above,
optionally in the presence of a reaction auxiliary and optionally in the presence of a diluent,
(b) converting the latter by adding hydrogen sulphide or salts thereof,
optionally in the presence of a reaction auxiliary and optionally in the presence of a diluent,
to 3-butenyl 1-dithiocarbamate of the formula (V)

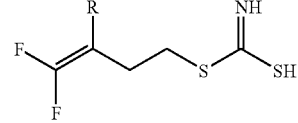

where
R is as defined above,
and
(c) finally reacting the latter, optionally in the presence of a reaction auxiliary and optionally in the presence of a diluent, with acetaldehyde, chloro-acetaldehyde ($ClCH_2CHO$) or acetals thereof, for example chloro-acetaldehyde dialkyl acetal. The acetals may also be cyclic acetals.

The process according to the invention has the advantage that the use of the unstable ammonium dithiocarbamate can be avoided. In contrast, the intermediates of the formulae (IV) and (V) are stable when stored. 3,4,4-Trifluoro-3-butenyl 1-dithio-carbamate of the formula (V) can be converted very easily using, for example, acetaldehyde, chloroacetaldehyde or acetals thereof to 2-[(3,4,4-trifluoro-3-butenyl)sulphanyl]-1,3-thiazole without the danger of decomposition and release of dangerous $CS_2$ and without the occurrence of resinous by-products as occur in the reaction of ammonium dithiocarbamate with chloroacetaldehyde. Such by-products are also mentioned in EP 0 926 140 A1. The use of the oxidation-sensitive 2-mercapto-1,3-thiazole used in the previous processes may be avoided. In the reaction of compounds of the formula (V) with (cyclic) acetals, the presence of an acid, for example HCl, p-toluenesulphonic acid or methanesulphonic acid, is of significance.

A further special feature of the process is the reaction of 3-butenyl thiocyanates of the formula (IV) with hydrogen sulphide or with salts thereof. Sulphur nucleophiles, for example $H_2S$, generally add to the double bond of fluorine-containing olefins (for example Ali et al. (1982), J. Med. Chem. 25, 1235). In the present invention, it was shown that $H_2S$ and salts thereof (reaction (b)) surprisingly add exclusively to the thiocyanate group and not to the olefin of compounds of the formula (IV). The reaction described likewise forms part of the subject-matter of the invention.

For the same reason, it may also be regarded as surprising that the reaction of a thiocyanate salt of the formula (III) ($M^+SCN^-$) with a compound of the formula (II) results only in the substitution of the X radical, and not in addition to the double bond. It was further not to be expected that the desired thiocyanate of the formula (IV) can be obtained by a reaction of compounds of the formula (II) with salts of thiocyanic acid of the formula (III). Rather, it has hitherto been known that reactions of alkyl halides with salts of thiocyanic acid lead frequently to the thermodynamically more stable isothiocyanates (cf. Houben-Weyl Vol. IX, p. 857 and p. 867). It can therefore be regarded as extraordinary that in the present case the desired regionisomer 3-butenyl thiocyanate is obtained exclusively. The reaction (a) described likewise forms part of the subject-matter of the present invention.

As an alternative to the above-mentioned process, it is also possible to react compounds of the formula (II) directly with ammonium dithiocarbamate ($H_2NCS_2NH_4$) to give 3-butenyl 1-dithiocarbamates of the formula (V).

The process according to the invention and also the above-mentioned alternative step can be represented schematically as follows:

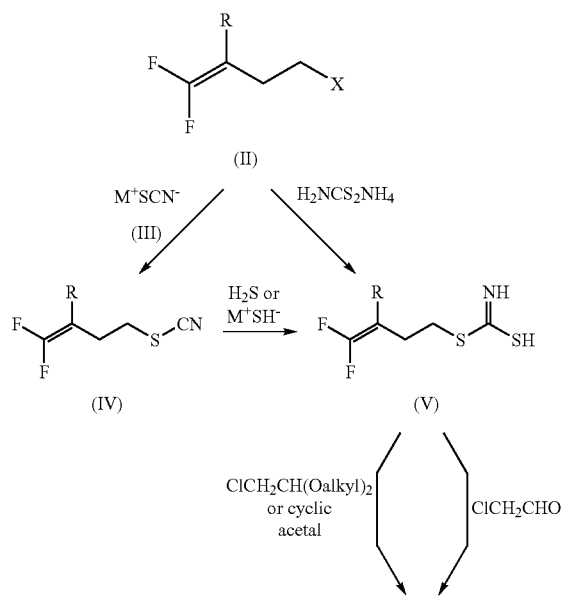

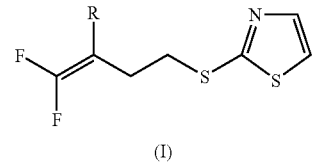

When, for example, 4-bromo-1,1,2-trifluoro-1-butene and ammonium thiocyanate are used, 3,4,4-trifluoro-3-butenyl thiocyanate is obtained which is then reacted with $H_2S$ to give 3,4,4-trifluoro-3-butenyl dithiocarbamate. Further reaction of 3,4,4-trifluoro-3-butenyl dithiocarbamate with chloroacetaldehyde then provides 2-[(3,4,4-trifluoro-3-butenyl)sulphanyl]-1,3-thiazole. This reaction sequence may be schematically represented as follows:

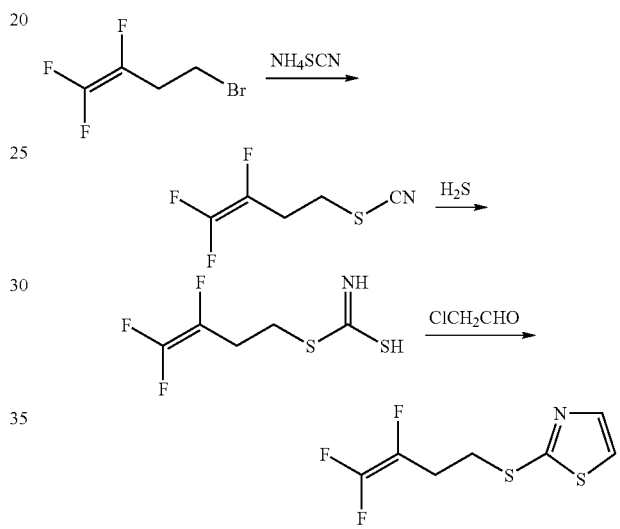

The process steps according to the invention may be carried out directly after one another or else individually, and the product in each case may also be purified.

The compounds used in the process (a) according to the invention to prepare the compounds of the formula (IV) are characterized by the formula (II). In the formula (II), X is more preferably bromine and R is particularly preferably fluorine. The compounds of the formula (II) are known compounds. Compounds of the formula (II) where X is F are described, for example, in WO 86/07590 and may be prepared by the process cited there. Compounds of the formula (II) where X is H are described, for example, in GB 2304713 and may be prepared by the process cited there.

The compounds further used in the process (a) according to the invention to prepare the compounds of the formula (IV) are characterized by the formula (III). In the formula (III), $M^+$ is preferably a potassium, sodium or ammonium ion, more preferably an ammonium ion. The thiocyanate salts of the formula (III), for example ammonium thiocyanate ($NH_4SCN$), are known compounds and are commercially available.

The compounds of the formula (IV) which are also starting materials for preparing the compounds of the formula (V) are novel substances which likewise form part of the subject-matter of the present application. In the formula (IV), R is preferably hydrogen or fluorine, more preferably fluorine.

The compounds of the formula (IV) may be prepared by the above-mentioned process (a). The preparation of trifluorobutenyl dithiocarbamates was described, for example, in U.S. Pat. No. 3,510,503 by reacting a 4-bromo-1,1,2-trifluoro-1-butene with, inter alia, a substituted ammonium dithiocarbamate, or, after condensing a suitable mercaptan and $CS_2$ under basic catalysis, adding 4-bromo-1,1,2-trifluoro-1-butene.

The compounds further used in the process (b) according to the invention to prepare the compounds of the formula (V) are hydrogen sulphide ($H_2S$) and salts thereof. These compounds may generally be described by the formulae MSH and $M_2S$ where $M^+$ is, for example, an ammonium ion or sodium ion. Preference is given to using $H_2S$, ammonium sulphide, NaSH solution or else $Na_2S$ in the process (b) according to the invention.

The ammonium salt of dithiocarbamic acid ($NH_2NCS_2NH_4$) usable in the alternative process according to the invention to prepare compound (V) starting from compounds of the formula (II) is known and also commercially available.

The chloroacetaldehyde and chloroacetaldehyde dialkyl acetals used in the process (c) according to the invention to prepare compounds of the formula (I) are known and commercially available.

The compounds further used in the process (c) according to the invention to prepare the compounds of the formula (I) are characterized by the formula (V). The compounds of the formula (V) are novel compounds which form part of the subject-matter of the present application. They may be prepared by the above-mentioned processes (b) or (a) and (b). The compounds of the formula (V) may be tautomers (see diagram above and Example 2).

Preference is given to carrying out the processes (a) to (c) according to the invention for preparing the compounds of the general formula (I) using diluents. Useful diluents for carrying out the process according to the invention, as well as water, are in particular inert organic solvents. These include in particular aliphatic, alicyclic or aromatic, optionally halogenated hydrocarbons, for example benzine, benzene, toluene, xylene, chlorobenzene, dichlorobenzene, petroleum ether, hexane, cyclo-hexane, dichloromethane, chloroform, carbon tetrachloride; ethers such as diethyl ether, diisopropyl ether, dioxane, tetrahydrofuran, 2-methyltetrahydrofuran, methyl t-butyl ether, ethylene glycol dimethyl ether or ethylene glycol diethyl ether; ketones such as acetone, butanone or methyl isobutyl ketone; nitriles such as acetonitrile, propionitrile or butyronitrile; amides such as N,N-dimethylformamide, N,N-dimethylacetamide, N-methylformanilide, N-methylpyrrolidone or hexamethyl-phosphoramide; esters such as methyl acetate or ethyl acetate; sulphoxides such as dimethyl sulphoxide; alcohols such as methanol, ethanol, n- or i-propanol, ethylene glycol monomethyl ether, ethylene glycol monoethyl ether, diethylene glycol monomethyl ether, diethylene glycol monoethyl ether or mixtures thereof with water.

Useful diluents for carrying out the process (a) are in particular protic polar solvents, for example alcohols such as methanol, ethanol, n- or i-propanol, ethylene glycol monomethyl ether, ethylene glycol monoethyl ether, diethylene glycol monomethyl ether or diethylene glycol monoethyl ether. In a particularly preferred embodiment, the diluent used is ethanol.

Useful diluents for carrying out the process (b) are in particular, for example, ethers such as diethyl ether, diisopropyl ether, methyl t-butyl ether, dioxane, tetrahydrofuran, 2-methyltetrahydrofuran, ethylene glycol dimethyl ether or ethylene glycol diethyl ether, pyridine, ethyl acetate or isopropyl acetate. In a particularly preferred embodiment, the diluent used is methyl tert-butyl ether.

Useful diluents for carrying out the process (c) are in particular, for example, dioxane, acetonitrile and carboxylic acids, for example glacial acetic acid, p-toluenesulphonic acid, methanesulphonic acid and mixtures thereof. Preference is also given to adding the carboxylic acids, p-toluenesulphonic acid or methane-sulphonic acid only in catalytic quantities.

Useful reaction auxiliaries for the processes (a) and (b) according to the invention are the generally customary inorganic or organic bases or acid acceptors. These preferably include alkali metal or alkaline earth metal acetates, amides, carbonates, hydrogencarbonates, hydrides, hydroxides and alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide or n-, i-, s- or t-butoxide, potassium methoxide, ethoxide, n- or i-propoxide or n-, i-, s- or t-butoxide; and also basic nitrogen compounds, for example ammonia, trimethylamine, triethyl-amine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- or 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

For the process (b), preference is given to using 0.1-20 mol % of base, more preferably 0.5-8 mol % of base.

Useful reaction auxiliaries for the process (c) according to the invention are in particular, for example, carboxylic acids, for example acetic acid, HCl, $BF_3$, $H_2SO_4$, trifluoroacetic acid, p-toluenesulphonic acid and methanesulphonic acid which are used directly as solvents but may also be added to the reaction in catalytic quantities. These are preferably 0.1 to 10 mol %, more preferably 0.5 to 5 mol %, of the reaction auxiliaries mentioned.

The reaction temperatures may be varied within a relatively wide range when carrying out the process according to the invention. In general, operation is effected at temperatures of 0° C. to 150° C., preferably 10° C. to 120° C. Preferred temperature ranges may also be inferred from the preparative examples.

The processes according to the invention are generally carried out under atmospheric pressure. However, it is also possible to carry out the processes according to the invention under elevated or reduced pressure—in general 0.1 bar to 50 bar, preferably 1 to 10 bar.

To carry out the process according to the invention, the starting materials are generally used in near equimolar quantities. However, it is also possible to use one of the components in a relatively large excess. When carrying out the process (b) according to the invention, preference is given to using 1.5 to 3 mol of hydrogen sulphide or of a salt thereof per mole of the compound of the formula (IV). The reaction is generally carried out in a suitable diluent in the presence of a reaction auxiliary and the reaction mixture is generally stirred for more than one hour at the temperature required. The workup is carried out by customary methods (cf. the preparative examples).

In a preferred embodiment of the process (a) according to the invention for preparing the compounds of the formula (IV), the thiocyanate of the formula (III) is stirred in a solvent, preferably an alcohol, with a compound of the formula (II), preferably at room temperature, and a precipitate forms. The batch is then heated to reflux and cooled, the filtrate filtered off with suction and concentrated by evaporation.

In a preferred embodiment of the process (b) according to the invention for preparing the compounds of the formula (V), hydrogen sulphide is passed gradually until saturation into a solution of the compound of the formula (IV), preferably in methyl t-butyl ether, in the presence of a base, preferably triethylamine, and then stirred. After evaporation of the solvent, the compound of the formula (V) is obtained.

In a preferred embodiment of the process (c) according to the invention for preparing the compounds of the formula (I), the compound of the formula (V) in a diluent, preferably dioxane, is admixed with an aqueous chloroacetaldehyde solution in the presence of a catalytic quantity of hydrochloric acid and boiled under protective gas. In a preferred embodiment of the process (c) according to the invention for preparing the compounds of the formula (I), the compound of the formula (V) in a diluent, preferably glacial acetic acid, is admixed with chloroacetaldehyde diethyl acetal in the presence of a catalytic quantity of p-toluenesulphonic acid monohydrate and stirred at elevated temperature. After cooling to room temperature, the mixture is concentrated by evaporation, the residue taken up in, for example, dichloromethane and washed with an alkaline solution, preferably 1 N sodium hydroxide solution, and the organic phase removed.

The compounds of the formula (I) are prepared according to the following examples which further illustrate the process steps (a), (b) and (c). However, the examples should not be interpreted in a limiting manner.

EXAMPLES

Example 1

Preparation of 3,4,4-trifluoro-3-butenyl thiocyanate (process (a))

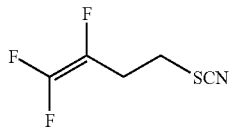

60.25 g (771.7 mmol) of ammonium thiocyanate in 400 ml of ethanol are admixed with 164.3 g (810.3 mmol) of 4-bromo-1,1,2-trifluoro-1-butene and stirred at room temperature for 2 h to form a white precipitate. The mixture is then boiled for 8 h to reflux. After cooling to room temperature, the filtrate is filtered off with suction and concentrated by evaporation under reduced pressure. The evaporation residue is taken up in dichloromethane, washed with water, dried over sodium sulphate and concentrated by evaporation under reduced pressure. 121.1 g (93.3% of theory; purity by GC/MS: 99.4 area %) of a yellow oil are obtained.

$R_f$(SiO$_2$, CH$_2$Cl$_2$): 0.85.

$^1$H NMR (CDCl$_3$, 400 MHz):δ=2.8-2.92 (m, 2H), 3.1 (t, 1H).

$^{13}$C NMR (CDCl$_3$, 100 MHz): δ=26.6 (CH$_2$—CF), 29.5 (S—CH$_2$), 110.9 (SCN), 125.4 (CF), 153.7 (CF$_2$).

MS (DCI,NH$_3$): 167 (11%, M$^+$), 108 (92%), 95 (100%), 69 (40%).

Example 2

Preparation of 3,4,4-trifluoro-3-butenyl dithiocarbamate (thio-cyanate process) (process (b))

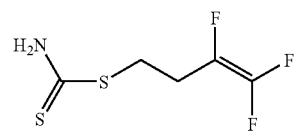

Hydrogen sulphide is passed gradually until saturation (about 2 molar equivalents) into a solution of 33.41 g (200 mmol) of 3,4,4-trifluoro-3-butenyl thiocyanate and a total of 0.26 g of triethylamine in 130 ml of methyl tert-butyl ether at 10° C., and the mixture is then stirred at room temperature overnight. After evaporating the solvent under reduced pressure, 41.2 g (88.5% of theory; purity by GC/MS: 86.4 area %) of a crystallizing residue are obtained which may be recrystallized from cold toluene.

m.p.: 49-53° C.

$R_f$(SiO$_2$, toluene-ethyl acetate 4:1): 0.5.

$^1$H NMR (CDCl$_3$, 400 MHz):δ=2.65-2.82 (m, 2H,), 3.41 (t, 2H), 6.7 (broad s, 1H), 7.25 (broad s, 1H).

MS (DCI,NH$_3$): 201 (0.2%, M$^+$), 119(50%), 93 (58%), 60 (100%).

Example 3

Preparation of 3,4,4-trifluoro-3-butenyl dithiocarbamate (ammonium dithiocarbamate process)

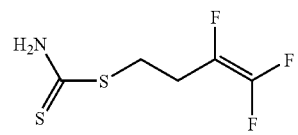

2.8 g (25 mmol) of ammonium dithiocarbamate in 40 ml of ethanol are admixed dropwise with 5.32 g (26.3 mmol; purity 93.2%) of 4-bromo-1,1,2-trifluoro-1-butene, stirred at 40° C. for 3 h, another 2.8 g of ammonium dithiocarbamate is added after 1 h, and everything is left to stand at room temperature for 8 h. The filtrate is filtered off with suction and concentrated by evaporation under reduced pressure, the residue taken up in dichloromethane and washed once with water, and the organic phase dried over sodium sulphate. After concentration by evaporation under reduced pressure, 4.3 g (63% of theory; purity by GC/MS: 74 area %) of a semicrystalline residue are obtained.

Example 4

Preparation of 2-[(3,4,4-trifluoro-3-butenyl)sulphanyl]-1,3-thiazole (process (c) using chloroacetaldehyde)

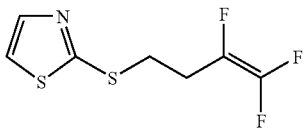

15.1 g (64.8 mmol; purity 86.3%) of 3,4,4-trifluoro-3-butenyl dithiocarbamate in 100 ml of dioxane are admixed with 0.2 ml of conc. hydrochloric acid and 12.4 g (71.2 mmol) of 45% aqueous chloroacetaldehyde solution. The mixture is boiled for 4 h under argon, and another 1 ml of chloroacetaldehyde solution is added after 2 h. The mixture is then concentrated by evaporation under reduced pressure, the residue taken up in dichloromethane and washed with water, and the organic phase concentrated by evaporation under reduced pressure after drying over $MgSO_4$. 16 g (94.4% of theory; purity by GC/MS: 86.1 area %) of an oil are obtained, which may be distilled at 0.4 T/86° C.

Example 5

Preparation of 2-[(3,4,4-trifluoro-3-butenyl)sulphanyl]-1,3-thiazole (process (c) using chloroacetaldehyde diethyl acetal)

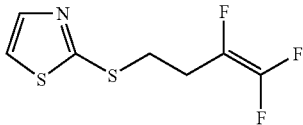

3 g (14.9 mmol) of 3,4,4-trifluoro-3-butenyl dithiocarbamate in 15 ml of glacial acetic acid are admixed with 2.3 g (15.1 mmol) of chloroacetaldehyde diethyl acetal and 40 mg of p-toluenesulphonic acid monohydrate. The mixture is stirred at 95° C. for 1.5 h and, after cooling to room temperature, is then concentrated by evaporation under reduced pressure. The evaporation residue is taken up in dichloromethane and washed with 1 N sodium hydroxide solution, and the organic phase is removed, dried over $Na_2SO_4$ and concentrated by evaporation under reduced pressure. 2.8 g (81.5% of theory; purity by GC/MS: 97.7 area %) of an oil are obtained.

What is claimed is:

1. A process for preparing a compound of formula (V)

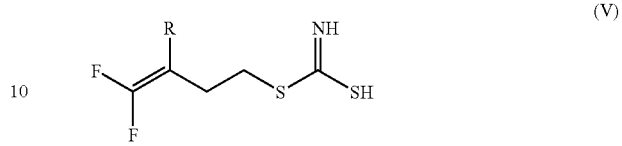

where R is H or F,
comprising reacting a compound of formula (IV)

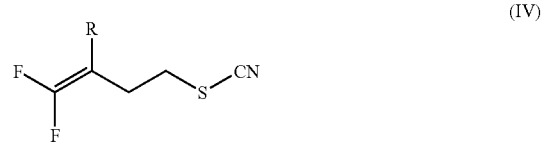

where R is H or F,
with hydrogen sulphide or salts thereof, optionally in the presence of a reaction auxiliary and optionally in the presence of a diluent.

2. A process according to claim 1 wherein the compound of formula (IV) is converted to the compound of formula (V) with $H_2S$.

3. A process according to claim 1 carried out in the presence of a base.

4. A process according to claim 2 carried out in the presence of a base.

5. A process according to claim 1 wherein R is fluorine.

6. A compound of formula (V)

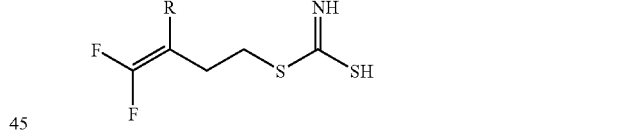

or a salt thereof,
where R is hydrogen.

* * * * *